United States Patent [19]

Enhorning

[11] Patent Number: 4,970,892
[45] Date of Patent: Nov. 20, 1990

[54] METHOD AND APPARATUS FOR DETERMINING SURFACE TENSION OR IF A SURFACTANT WILL KEEP A NARROW PASSAGEWAY OPEN

[76] Inventor: Goran E. Enhorning, 21 Oakland Pl., Buffalo, N.Y. 14222

[21] Appl. No.: 437,060

[22] Filed: Nov. 15, 1989

[51] Int. Cl.$^5$ ............................................. G01N 13/02
[52] U.S. Cl. ..................................................... 73/64.4
[58] Field of Search .......................................... 73/64.4

[56] References Cited

U.S. PATENT DOCUMENTS 2,054,438  9/1936  Natelson ............................. 73/64.4
3,854,324 12/1974  Altshuler et al. ................. 73/64.4 X Primary Examiner—Hezron E. Williams
Assistant Examiner—Joseph W. Roskos
Attorney, Agent, or Firm—Hodgson, Russ, Andrews, Woods & Goodyear

[57] ABSTRACT

A method and apparatus for determining if a surfactant will keep a narrow passageway open. The apparatus includes a glass tube having first and second end portions and an intermediate necked-down portion including a relatively narrow center and tapered first and second sections to either side of the relatively narrow center. In accordance with the method, a small quantity of fluid, for example one microliter, is placed within the necked-down portion to form a column of fluid. A pressure transducer is associated with a closed portion of the tube to one side of the column. The column of fluid is then slowly forced through the necked-down portion and the pressure is recorded. By continuing the process even after the column of fluid has passed the necked-down portion, it is possible to determine whether or not the fluid will adhere to the surface of the glass tube or re-form into a column of liquid. If the later happens, it is also possible to determine the surface tension of the fluid.

14 Claims, 2 Drawing Sheets

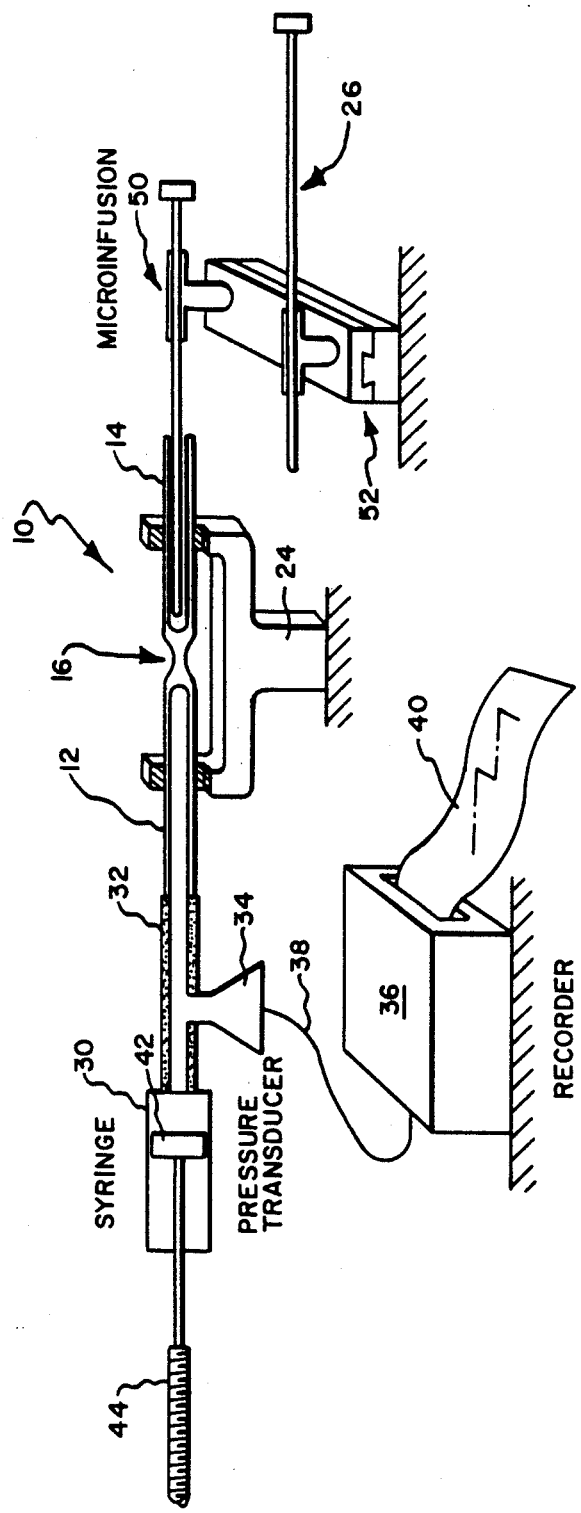

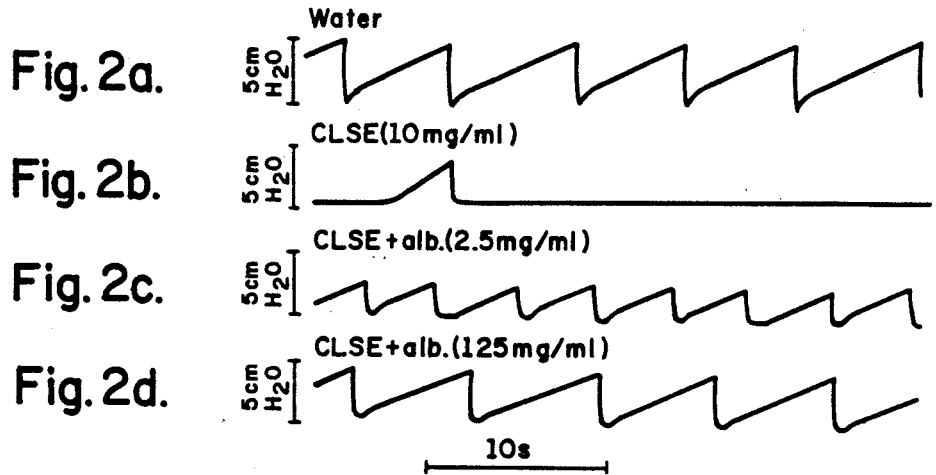
Fig. 2a. Water
Fig. 2b. CLSE (10 mg/ml)
Fig. 2c. CLSE + alb. (2.5 mg/ml)
Fig. 2d. CLSE + alb. (125 mg/ml)
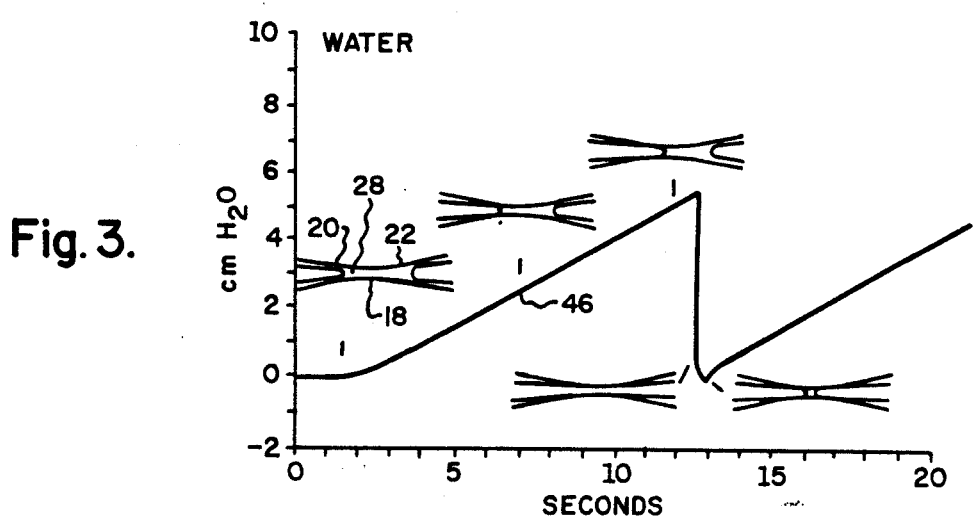
Fig. 3.
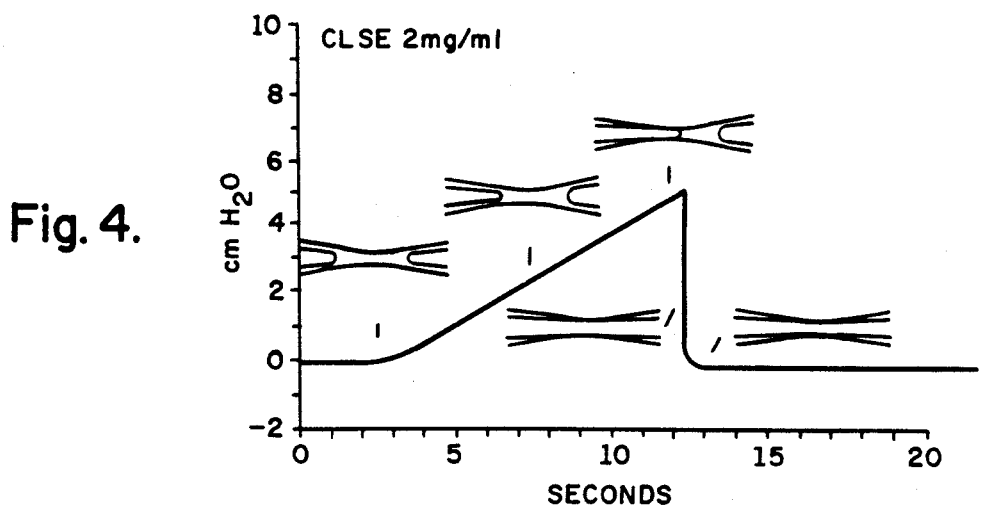
Fig. 4.

METHOD AND APPARATUS FOR DETERMINING SURFACE TENSION OR IF A SURFACTANT WILL KEEP A NARROW PASSAGEWAY OPEN

TECHNICAL FIELD

The present invention relates generally to a method and apparatus for determining surfactant capabilities, and more particularly to the ability of a fluid, with or without modifying surfactants, to form a film so that a narrow passageway is kept open. The present method and apparatus can also be used to determine surface tension.

BACKGROUND OF THE INVENTION

Various apparatus and procedures are well known in the art for determining surface tension. One such process is known as the maximum bubble pressure method. This process is described in Arthur W. Adamson's *Physical Chemistry of Surfaces*, 4th Edition, published by John Wiley and Sons, 1982, on page 18. This process requires a relatively large volume of fluid.

Apparatus known for determining surface tension includes the Wilhelmy balance which is available from the Kahn Company. Another apparatus is the Pulsating Bubble Surfactometer apparatus available from the Electronetics Corporation. The Wilhelmy balance apparatus will not tell whether or not a preparation of pulmonary surfactant has the ability to keep a narrow tube open. Furthermore, it is slow, requires a relatively large volume of fluid, and the cleaning procedures are laborious. The Pulsating Bubble Surfactometer apparatus has the disadvantage that it will not tell whether or not a preparation of pulmonary surfactant is able to keep a narrow tube open, and furthermore it requires a large volume of at least 25 microliters.

OBJECT AND SUMMARY OF THE INVENTION

It is an object of the present invention to provide a method and apparatus for determining a liquid's surface tension. The present invention is a variation or development of the maximum bubble pressure method. It is similarly accurate, but requires a sample volume of only one microliter.

The principle of the "maximum bubble pressure" method is to determine the pressure needed to force a hemispherical air-liquid interface through a narrow capillary. The air-liquid interface, or the meniscus, is made to move in the direction of the liquid, which helps to maintain its hemispherical shape. The capillary is usually vertical with its tip dipping into the liquid who's surface tension is to be determined. Pressure is continuously raised until the meniscus comes to the capillary's lower tip, where the radius is R. As a bubble forms, and the radius of the spherical surface can suddenly increase, pressure drops almost instantaneously. Pressure has thus reached a maximal value just before it drops conspicuously as a bubble is formed. If the radius at the capillary tip is known, surface tension $v$, can readily be calculated with the law of Laplace, $P = 2\mu/R$, since pressure, $P$, when the meniscus came to the capillary tip is known with exactness. Pressure is preferably recorded and has to be corrected for the hydrostatic pressure which has to be exerted because the capillary tip was under the surface of the liquid studied.

It is not necessary to know the radius at the capillary tip if the system is calibrated with a reference liquid with known surface tension.

The present invention differs from the conventional "maximum bubble pressure" method in that the capillary used does not have the same inner bore throughout its length. Furthermore, the capillary is not dipped into the liquid being examined. Instead, the capillary has a narrow section or a necked-down portion, which is filled with one microliter of the liquid to be studied. Due to surface tension, the liquid will tend to stay in the narrow section with interfaces towards the air, meniscii, which have the shape of sectors of a sphere, with the concavities towards the air.

One end of the capillary is connected with a pressure transducer and with an air-filled syringe. The piston of the latter is made to move slowly in either direction, preferably with a Harvard pump. Pressure, measured with the transducer, is seen to either increase or decrease. In case pressure is raised, the meniscus facing the enclosed end of the capillary will slowly be forced to move towards the section of the capillary where the radius is of minimal value. As soon as the meniscus has passed that section, pressure will very rapidly fall, just as when a bubble is formed with the "maximum bubble pressure" method. In case the piston of the air-filled syringe moved in the other direction, the liquid column would also be moving in the other direction, towards the air-filled syringe. Pressure would then be continuously lowered, until the other meniscus passed the most narrow section of the capillary. Abruptly pressure would then rise. Resistance to the liquid column's movement will primarily be due to surface tension in the small meniscus as it moves into the capillary's most narrow section. However, resistance will also be encountered from the other meniscus moving into a continuously widening section of the capillary. If the volume of liquid was exactly one microliter and the reference liquid had the same volume, the peak pressure recorded with the two liquids are related to each other as are the surface tensions.

It is a further object of the present invention to provide a method and apparatus for determining whether a fluid to forming a column in a narrow section of a capillary, will spread out on the wall of the capillary and, for a reasonable period, not form a new column of liquid in the narrow section once air has moved through that section. For example, it may be desirable to demonstrate how pulmonary surfactant will cause a narrow tube, and thus a narrow section of a cylindrical airway, such as a respiratory bronchiole, to stay open. Furthermore, it may be desirable to demonstrate that when the surfactant is deficient (either because its quantity is inadequate or because it is inhibited by proteins) it is not capable to keep the airway open, but a column of liquid reforms in the most narrow section of the tube. When surface tension is determined, as described above, the column of liquid in the narrow section of the capillary is forced to move, either by raising or by lowering pressure at one end of the capillary. One meniscus of the liquid column will hereby be forced to move towards the most narrow section of the glass tube. When the meniscus passes the most narrow section, pressure will suddenly change as the liquid spreads out on the inner wall of the widening glass tube. Most liquids, like water and alcohol, will almost instantaneously form a new liquid column in the most narrow section of the tube. This reforming of the liquid column can be directly observed through a microscope. It can also be deduced that a new liquid column has formed, since there is not longer a freed flow of air, but pressure is being raised or lowered by movement of the syringe piston. If a new liquid column is not formed, probably due to the extremely fast adsorbtion of a surface film with a surface pressure so high that it prevents the opening aperture to diminish in size.

Finally, it may also be desirable to demonstrate, that when inhibiting components, such as certain proteins, are added to a surfactant column, the latter will form again after being forced out from the narrow section of the capillary. Inversely, when a small volume of surfactant with high activity is added to a column of surfactant, which has demonstrated poor activity, the column will no longer reform but the capillary will remain open, allowing a free flow of air, i.e., pressure will not change.

The foregoing objects and other objects and advantages of this invention will become more apparent after consideration of the following detailed description taken in conjunction with the accompanying drawings.

BRIEF DESCRIPTION OF THE DRAWINGS

FIG. 1 is a somewhat schematic illustration of a preferred form of the present apparatus.

FIGS. 2a, 2b, 2c, and 2d illustrate various chart results for various fluids under analysis.

FIG. 3 represents a portion of the chart shown in FIG. 2a and further illustrates the condition of the fluid within the narrowest portion of the glass capillary at various positions with respect to various time intervals.

FIG. 4 is a view similar to FIG. 3 but illustrating the fluid which produced the graph shown at 2b.

DETAILED DESCRIPTION

As previously indicated, one of the purposes of the method and apparatus of this invention, is to determine whether a lung surfactant will keep an airway passage open, such as a respiratory bronchiole. Therefore, in the following detailed description, reference will be made to such a study.

As the epithelium of the respiratory bronchiole is hydrophilic and since this airway is of a very small diameter, it is necessary to provide comparable materials for study purposes. Glass is a material which is hydrophilic like the epithelium of the respiratory bronchiole. It can be obtained in various desired shapes and sizes with small tolerance variations. Since it is transparent, it is possible to photograph a column of liquid inside the glass tube with optimal sharpness. Thus, a glass tube, indicated generally at 10, is used as a passageway defining structure. The passageway has first and second end portions 12, 14 and an intermediate necked-down portion 16. The intermediate necked-down portion includes a relatively narrow center 18 (FIG. 3), and tapered first and second sections 20, 22 to either side of the relatively narrow center. The passageway defining means is preferably mounted horizontally in a stand which, for purposes of illustration, is shown as a saddle-type structure 24. The passageway defining means 10 was manufactured from glass capillaries that were used for measuring 100 microliters. Within a short section the glass tube was heated until it became soft and could be extended. In this way the capillary, which originally had an inner diameter of 1.19 millimeters, was given a narrow section where the diameter was only 0.4 millimeters. The passageway tube 10 is mounted in such a manner that the second end portion 14 is open to atmosphere. In order to properly test the fluid which is to be studied, it is necessary to place a very small quantity in the necked-down portion 16. Thus, approximately 1 microliter of fluid is initially instilled in the center of the necked-down portion, the material being instilled by means of a very narrow capillary, similar to those used for puncture of kidney glomeruli. The very narrow capillary, which is indicated generally at 26, is caused to be shifted into the open end 14 until it is properly located so that one microliter of the fluid to be studied can be placed in the very narrow portion. Incidentally, it should be noted that this quantity of fluid, which is very small, is far less than that required by the maximum bubble pressure method, a relatively well-known process for determining the surface tension of fluids. As can best be seen from FIG. 3, the fluid which is initially instilled will form a column 28. The column will have hemispherical air-liquid interfaces or menisci at each end. This is due to surface tension which is the phenomenon, due to molecular forces, existing in the surface film of all liquids which tends to contract the volume into a form with the least surface area. The particles of the surface film are inwardly attracted, thus resulting in tension. As can be seen, the liquid column within the narrow portion of the passageway will block the flow of air or other gases through the passageway.

In accordance of the principles of this invention, the liquid column is slowly forced along the necked-down portion 16 until a meniscus passes the central portion 18. After the meniscus passes the central portion 18, it will become wider and rupture, and the fluid will form into a ring at this time. The column can be forced to move by either slowly creating a vacuum in the end 12, or alternatively, and more preferably, by slowly increasing the pressure in the closed end 12 to force the column to the right as viewed in FIGS. 1, 3, and 4. Thus, as the left-hand meniscus passes the narrow portion 18, it will rupture. This will substantially instantaneously reduce the pressure within the closed-end portion of the tube 12.

The pressure is introduced into the closed end 12 by connecting the tube 10 to a syringe 30 by an intermediate tube 32 which is provided with a pressure transducer 34. The pressure transducer is in turn interconnected with a recorder 36 by line 38, or by other suitable means, and the recorder will produce a suitable chart indicated at 40.

Let us assume that water, which has a high surface tension, is tested. One microliter of water, which is a very small quantity as previously indicated, will be initially introduced into the necked-down portion 16. The plunger 42 within the syringe 30 will be preferably in its left-hand position. The syringe will be filled with air before the microliter of water is placed within the tube. After the microliter of water has been placed within the necked-down portion 16, the plunger 42 will be caused to be slowly advanced to the right by any suitable mechanism, such as the screw indicated at 44, or more preferably by a Harvard pump (not shown). As the plunger 42 is moved to the right, the pressure within the tube 32 will slowly build up and slowly force the column of fluid within the necked-down portion 16 right. The pressure will be recorded during this operation, and this will form the pressure line 46. At various positions the column of fluid can be photographed with suitable photographic equipment and various "snapshots" of the fluid column with respect to specific time intervals are illustrated in FIG. 3. As the meniscus passes the most narrow section of the necked-down portion 16, it will rupture permitting air to flow through the column substantially instantaneously reducing the pressure that has built up within the tube 32. If water is the substance being tested, it will again re-form a liquid column as shown at the lower right-hand "snapshot" FIG. 3 and then the process will be repeated again and again as can be seen by the Chart 2a.

The peak pressure, $\Delta P$, will make it possible to calculate surface tension, $\nu$, according to the law of Laplace, $\Delta P = 2\nu/R$.

One surfactant tested during the study is calf-lung surfactant extract (hereinafter CLSE), and a test of CLSE is shown in Chart 2b and also in FIG. 4. Again, one microliter of fluid was initially introduced into the necked-down portion 16. The syringe plunger was then progressively advanced to the right until the left-hand meniscus expanded and ruptured, this causing a substantial instantaneous pressure drop, as shown by the nearly vertical line 48 in FIG. 4. After the meniscus ruptured and the pressure dropped, the CLSE formed a film which adhered to the walls of the very narrow passageway, even at the central point 18 and a liquid column did not re-form during the test interval. The CLSE tested in FIG. 2b was of a 10 mg per milliliter concentration.

From the above descriptions two extreme situations have been illustrated, one where water has been used and the ring of liquid which is formed after the meniscus is ruptured having the characteristic where it would very quickly diminish its aperture and would transform into a column of liquid. This liquid column would put an end to the flow of air and pressure would start increasing again as shown in Chart 2a and reach the same peak value over and over again. This makes it possible to determine surface tension very accurately, as accurately as with the maximum bubble pressure method but using only one microliter. Many concentrations of methyl alcohol have been examined and the values of the surface tension are extremely close to those given by standard handbooks. The other extreme is where CLSE is used wherein the ring of liquid does not diminish its aperture and the flow of air through the ring, after the original meniscus has ruptured, will continue.

It may be desirable to modify the fluid being tested. This can be done by introducing very small quantities of fluid modifiers through a microinfuser, indicated generally at 50. The microinfuser is also a very small micro pipette which is capable of placing very small quantities of additional materials within the tube 10. Thus, for example, it may be desirable to micro-infuse as little as 0.15 microliters of additional material. Both the microinfuser 50 and the pipette 26 are shown mounted on a slide-block assembly 52. However, the slide block has only been shown for purposes of illustration and in fact these devices are supported by micromanipulators. Chart 2c and 2d show test results where small quantities of a protein has been added to CLSE, the protein being albumin. In 2c there is 10 mg of CLSE and 2.5 mg albumin per milliliter and in Chart 2d there is 10 mg of CLSE and 125 mg albumin per milliliter.

It can be seen from the foregoing that an apparatus for and a method of determining if a surfactant will keep a relatively narrow passageway open has been developed which has utility, particularly, when analyzing lung surfactants. Obviously there may be other utilities in addition to those described above and accordingly, this invention is not to be limited to the particular details shown and described above.

What is claimed is:

1. A method for determining surface tension or if a surfactant will keep a narrow passageway open comprising:
    (a) providing elongated passageway defining means, the passageway having first and second end portions, and an intermediate necked-down portion including a relatively narrow center and tapered first and second sections to either side of the relatively narrow center, the first and second tapered sections being adjacent to the first and second end portions, respectively, and one of the first and second end portions being open to atmosphere, and the other end portion not being open to atmosphere;
    (b) instilling a small quantity of the fluid whose surface tension is to be determined within the necked-down portion to form a column of fluid with first and second menisci within the first and second tapered sections, respectively, the menisci being spaced equally to either side of the narrow center when the gas pressure within the first and second end portions are equal;
    (c) creating and progressively increasing a pressure differential between the gases in the first and second end portions by either slowly introducing additional gas under pressure into the other end portion or by slowly withdrawing gas from the other end portion to cause the column of fluid to be slowly forced along the necked-down portion until the first meniscus passes the relatively narrow center, the first meniscus rupturing after it passes the relatively narrow center to open up the column of fluid to permit the gas pressure within the first and second end portions to substantially instantaneously equalize;
    (d) continuing to either slowly introduced additional gas under pressure into the other end portion or to slowly withdraw gas from the other end portion for a significant period of time after the first meniscus ruptures; and
    (e) recording the pressure within the other end portion.

2. The method as set forth in claim 1 further comprising the subsequent steps of adding a small quantity of surface tension modifying fluid to the fluid instilled in step b and subsequently repeating steps c and d to test the effect of the surface tension modifying liquid.

3. A method for determining surface tension or if a surfactant will keep a narrow passageway open comprising:
    (a) providing elongated passageway defining means, the passageway having first and second end portions, and an intermediate necked-down portion including a relatively narrow center and tapered first and second sections to either side of the relatively narrow center, the first and second tapered sections being adjacent to the first and second end portions, respectively, and one of the first and second end portions being open to atmosphere, and the other end portion not being open to atmosphere;
    (b) instilling a small quantity of the fluid whose surface tension is to be determined within the necked-down portion to form a column of fluid with first and second menisci within the first and second tapered sections, respectively, the menisci being spaced equally to either side of the narrow center when the gas pressure within the first and second end portions are equal;

(c) progressively increasing the pressure of the gas within the first end portion by slowly introducing additional gas under pressure into the other end portion to cause the column of fluid to be slowly forced along the necked-down portion until the first meniscus passes the relatively narrow center, the first meniscus rupturing after it passes the relatively narrow center to open up the column of fluid to permit the gas pressure within the first and second end portions to substantially instantaneously equalize;

(d) continuing to introduce additional gas under pressure into the other end portion for a significant period of time after the first meniscus ruptures; and (e) recording the pressure within the other end portion during steps c and d.

4. The method as set forth in claim 3 further comprising the subsequent steps of adding a small quantity of surface tension modifying fluid to the fluid instilled in step b and subsequently repeating steps c and d to test the effect of the surface tension modifying fluid.

5. Apparatus for determining surface tension or if a surfactant will keep a narrow passageway open comprising:

(a) elongated passageway defining means, the passageway having first and second end portions, and an intermediate necked-down portion including a relatively narrow center and tapered first and second sections to either side of the relatively narrow center, the first and second tapered sections being adjacent to the first and second end portions, respectively, and one of the first and second end portions being open to atmosphere, and the other end portions not being open to atmosphere;

(b) means for instilling a small quantity of the fluid whose surface tension is to be determined within the necked-down portion to form a column of fluid with first and second menisci within the first and second tapered sections, respectively, the menisci being spaced equally to either side of the narrow center when the gas pressure within the first and second end portions are equal;

(c) means for creating and progressively increasing a pressure differential between the gases in the first and second end portions; and (d) means for recording the pressure within the other end portion.

6. The apparatus as set forth in claim 5 wherein the means for creating and progressively increasing a pressure differential includes means for introducing gas under pressure into the other end portion.

7. The apparatus as set forth in claim 6, wherein the means for creating and progressively increasing a pressure differential is a syringe.

8. The apparatus as set forth in claim 5 wherein the elongated passageway defining means is formed of a hydrophilic material.

9. The apparatus as set forth in claim 8 wherein the hydrophilic material is a glass tube.

10. The apparatus as set forth in claim 9, wherein the relatively narrow center of the necked-down portion has a diameter of approximately 0.4 mm.

11. The apparatus as set forth in claim 5 wherein the apparatus is further characterized by the provision of means for adding a small quantities of surface tension modifying fluid to the fluid initially instilled in the elongated passageway.

12. The apparatus as set forth in claim 11 wherein the means for adding a small quantity of surface tension modifying fluid is a very narrow bore pipette.

13. The apparatus as set forth in claim 5 wherein the relatively narrow center of a necked-down portion has a diameter of approximately 0.4 millileter.

14. The apparatus as set forth in claim 5 wherein the means for creating and progressively increasing a pressure differential is a syringe.

* * * * *